(12) United States Patent
Dybas et al.

(10) Patent No.: US 6,331,300 B1
(45) Date of Patent: Dec. 18, 2001

(54) COMPOSITIONS FOR PROVIDING A CHEMICAL TO A MICROORGANISM

(75) Inventors: Michael J. Dybas; Craig S. Criddle, both of Lansing; Michael E. Witt, Holt, all of MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/177,248

(22) Filed: Oct. 22, 1998

Related U.S. Application Data

(62) Division of application No. 09/061,305, filed on Apr. 16, 1998, now Pat. No. 6,287,846.
(60) Provisional application No. 60/044,090, filed on Apr. 21, 1997.

(51) Int. Cl.[7] ................ B09B 3/00; C02F 3/00; C12N 1/12; C12N 1/20
(52) U.S. Cl. ............ 424/93.4; 210/601; 210/610; 424/400; 424/484; 424/489; 435/252.1; 435/262.5
(58) Field of Search .................. 210/601, 610; 435/262.5, 252.1; 424/93.4, 400, 484, 489

(56) References Cited

U.S. PATENT DOCUMENTS

| | | |
|---|---|---|
| 3,224,946 | 12/1965 | Raymond . |
| 4,039,438 | 8/1977 | Anderson . |
| 5,265,674 | 11/1993 | Fredrickson et al. . |
| 5,268,109 | 12/1993 | Boyd . |
| 5,299,638 | 4/1994 | Cheneviere et al. . |
| 5,340,376 | 8/1994 | Cunningham . |
| 5,348,803 | 9/1994 | Schlaemus et al. . |
| 5,401,413 | 3/1995 | Gatt et al. . |
| 5,560,737 | 10/1996 | Schuring et al. . |
| 5,602,036 | 2/1997 | Criddle et al. . |
| 5,730,550 | 3/1998 | Andersland et al. . |

OTHER PUBLICATIONS

Tatara, et al., Applied Environmental Microbiology, vol. 59, pp. 2126–2131 (1993).

Markwell, et al., Methods of Enzymology, vol. 72, pp. 296–301 (1981).

Criddle, et al., Applied Environmental Microbiology, vol. 56, pp. 3240–3246 (1990).

Dybas, et al., Applied Environmental Microbiology, vol. 61, pp. 758–762 (1995).

Fletcher et al, Applied Environmental Microbiology, vol. 58, pp. 2954–2959 (1992).

*Primary Examiner*—Michael G. Wilyehyn
(74) *Attorney, Agent, or Firm*—Ian C. McLeod

(57) ABSTRACT

A method and composition for microbial remediation or other treatment of chemicals is described. The method particularly uses solidified oils or oils impregnated into inert particles or particles which release nutrient medium over time.

11 Claims, 5 Drawing Sheets

COMPOSITIONS FOR PROVIDING A CHEMICAL TO A MICROORGANISM

This application is a divisional of application Ser. No. 09/061,305, filed Apr. 16, 1998 now U.S. Pat. No. 6,287, 846, and claims priority to provisional application Ser. No. 60/044,090, filed Apr. 21, 1997.

BACKGROUND OF THE INVENTION (1) Field of the Invention

The present invention relates to a method using particles for providing pre-selected amounts of a chemical to a microorganism over time. In particular, the present invention relates to a particle for delivery of a nutrient to a microorganism which is released in small amounts over time from the particle. The method is particularly useful for bioremediation of contaminated sites in situ.

(2) Description of Related Art

There is a need to deliver chemicals over time to a microorganism. The purpose can be to produce a chemical, such as an enzyme, or drug or to facilitate the growth of the microorganism.

Toxic compounds contaminating the environment can be converted into innocuous substances by microbial digestion of the toxic substances, referred to as bioremediation. Bioremediation has been used to treat soil in above-ground treatment systems, above-ground bioreactors, slurry pits, above-ground soil heaps, compositing material, and in subsurface systems in situ.

The current methods for introducing remediation compositions into contaminated environments include injection of liquid or gas phase components into subsurface environments, extraction of liquid or gas phase components and treatment ex situ, or excavation of contaminated sites for treatment ex situ. These methods are labor intensive and expensive. It will become apparent that the prior art does not provide for an inexpensive, versatile and effective means for in situ remediation. The most closely related prior art is as follows.

U.S. Pat. No. 3,224,946 to Raymond relates to the use of zeolites to absorb the hydrocarbons to be degraded and then degrading the hydrocarbon with the microorganism. Specifically, this method uses hydrous aluminosilicate to act as a molecular sieve whereby hydrocarbonaceous material may become lodged until the material is released by chemical conversion by a bacteria. The method provides for an in vitro means for degrading hydrocarbonaceous material ex situ.

U.S. Pat. No. 4,039,438 to Anderson describes the use of pulp or paper as a substrate with bacteria to reduce nitrate in water.

U.S. Pat. No. 5,268,109 to Boyd describes the use of clays which have been ion exchanged to remove contaminants. The method does not relates to in situ remediation.

U.S. Pat. No. 5,265,674 to Frederickson et al relates to the introduction of oils and nutrients and optimally microorganisms into a zone to be remediated. The method effects remediation by pumping liquid oil into a contaminated site and allowing the oil to move throughout the soil concentrating and absorbing the contaminants. The oil containing the contaminants is then removed from the soil. An additional method proves for the addition of microbes to the oil applied to the site and allowing the microbes to degrade the contaminants concentrated by the oil. A limitation of this method is that the oil is applied to the remediation zone in liquid form. In liquid form, the dissolution of the oil is fairly rapid therefore, requiring repeated applications to effectively remove the contaminants.

U.S. Pat. No. 5,299,638 to Cheneviere et al relates to the use of clays or other porous materials with bacteria to produce viscosity promoting polymers.

U.S. Pat. No. 5,340,376 to Cunningham relates to the controlled release of nutrients with a timed release coating. Once the coating is gone, the nutrient is released. The invention provides for remediation by providing nutrients for the bacteria fauna already present which then degrade the contaminating organic compounds. The nutrients are provided as granules of urea coated with a resin which when introduced into a site continuously provide nutrients for up to three months. The limitation of the invention is that it relies on the naturally occurring bacteria fauna already present at the contaminated site. If the site does not provide the bacterial species that are capable of degrading the offending contaminant or in sufficient numbers then the invention will not be effective for remediation. Furthermore, the composition and method were designed for surface level remediation wherein the composition is tilled into the soil.

U.S. Pat. No. 5,348,803 to Schlaemus et al relates to microcapsules of microorganisms and hydrocarbons as nutrients. This invention is an improvement over the previous invention in that capsules having a water insoluble coating containing a microorganism capable of degrading hydrocarbons surrounds a core that provides nutrients for the microorganism. The invention is designed to be sprayed on oil spills in an aqueous environment whereby the microcapsules being water insoluble remain associated with the oil.

U.S. Pat. No. 5,401,413 to Gatt et al relates to microorganisms and exposures for bioremediation. The invention provides a composite material having a core containing water soluble microbial nutrients and a partially oil soluble and biodegradable coating. The composite material is sprayed or dusted onto an oil spill whereby the oil soluble coating causes the composite to associate with the oil contamination.

U.S. Pat. No. 5,602,036 to Criddle et al relates to metabolites of Pseudomonas which enhance bioremediation. Metabolites produced by Pseudomonas are introduced into a material containing a halogenated hydrocarbon and an indigenous or added bacterium to effect degradation of the halogenated hydrocarbon by the bacterium.

U.S. Pat. No. 5,560,737 to Schuring et al relates to pneumatic fracturing and introduction of microorganisms or nutrients into the fracture.

U.S. Pat. No. 5,730,550 to Andersland et al describes the use of a freeze wall for placement of a bioremediation method in situ.

The problem with this prior art is that an effective method for placement of the long term or time (months) released nutrients and/or microorganisms in situ is not described. This limitation and other limitations of the prior art will become more apparent from the discussion that follows.

OBJECTS

It is therefore an object of the present invention to provide novel forms of particles which release nutrients over time as needed by the microorganisms. It is further an object of the present invention to provide a method which is easy to perform and which is economical. These and other objects of the present invention will become increasingly apparent by reference to the following description and the drawings.

DESCRIPTION OF PREFERRED EMBODIMENTS

Figure 1:
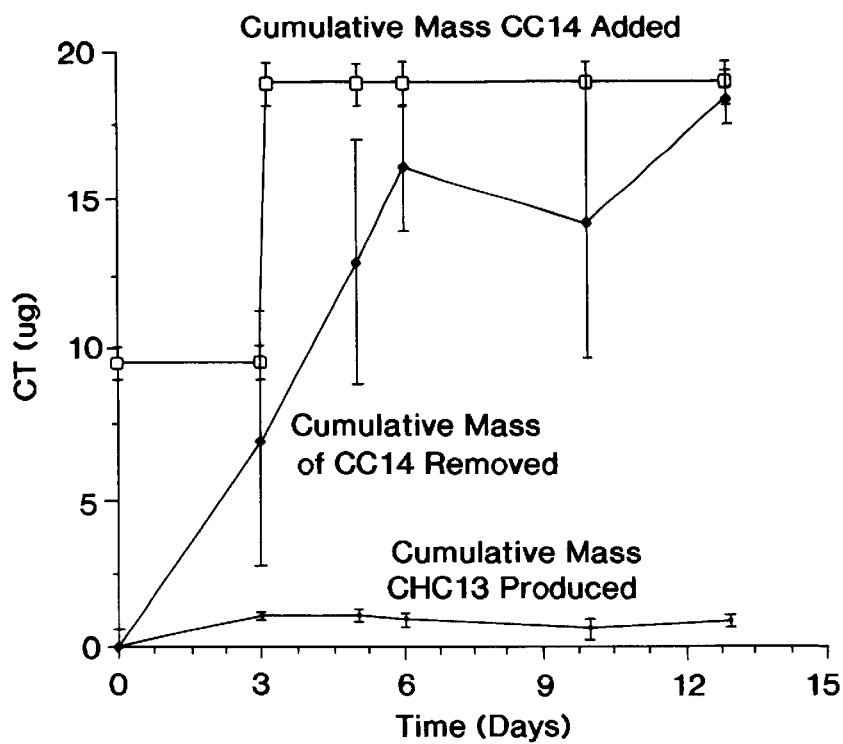
FIG. 1 is a graph showing the cumulative mass of $CCl_4$ removed and $CHCl_3$ produced by *P. stutzeri* KC using a prior art method. $CCl_4$ was added initially and on day 3. Error bars for the mass of $CCl_4$ added represent the cumulative error of addition. Error bars for experimental samples represent a standard deviation of three independently grown cultures. The graph shows that this method is particularly effective.

The present invention relates to a method for providing a chemical to a microorganism over time which comprises: providing particles containing the chemical utilizable by a microorganism and exposed on a surface of each of the particles, wherein particle can release the chemical over an extended period of time to the microorganism in water; and introducing the particles in the presence of water, so that the microorganism is able to utilize the chemical.

The present invention relates to a method for providing a chemical to a microorganism over time, which comprises: providing particles which comprise an inert and water insoluble particle having multiple channels which are less than about 0.1 to 100 microns in average diameter and having a size of about 0.1 to 50 millimeters; and a chemical provided in the channels which is utilizable by the microorganism, which chemical is exposed on the surface of each of the particles and is released over time from the particle in an aqueous environment to be utilized by the microorganism; and introducing the particle into the aqueous environment with the microorganism so that the chemical is released to the microorganism.

The present invention also relates to a method for remediating a zone of contamination in situ in the earth containing water by injecting a nutrient medium for a microorganism into the zone, the improvement which comprises: injecting the nutrient medium into the zone in particles with the nutrient medium exposed on a surface of each of the particles, and within the channel structure and which release the nutrient medium into the water in the zone so that microorganisms in the zone are provided with the nutrient medium over an extended period of time.

The present invention relates to a composition which comprises multiple particles which are impregnated with one of (1) a microorganism which chemically modifies a compound, (2) an electron acceptor, (3) an electron donor, (4) substances for modification of pH or (5) a nutrient medium for the microorganism which are exposed on a surface of each of the particles and are releasable over time in situ in an aqueous environment.

The present invention relates to a composition which comprises particles containing a nutrient medium for a microorganism exposed on a surface of the particles, wherein the particles release at least two chemicals on separate particles over an extended period of time to the microorganism in the presence of water.

The present invention relates to particles for providing a chemical to a microorganism over time which comprises: inert and water insoluble particles having multiple channels which are less than about 0.1 to 100 microns in average diameter and having a size of about 0.1 to 50 millimeters; and a chemical provided in the channels which is utilizable by the microorganism, which is exposed on a surface of the particles and which is released over time from the particles in an aqueous environment to be utilized by the microorganism.

DEFINITIONS

Bioremediation—The term "bioremediation" means the process of treating a noxious substance (a toxic or unwanted chemical or compound) with a microorganism that is capable of digesting, detoxifying, or converting the chemical or compound to a less toxic or non-toxic chemical or compound thereby removing the offending substance.

Contaminant—The term "contaminant" means a composition which is environmentally unwanted in soil or water. Examples of contaminants are organic chemicals such as carbon tetrachloride, nitrates, aliphatic hydrocarbons, aromatic hydrocarbons, including halogenated aromatic, polynuclear aromatic, polychlorinated biphenyl, trichloroethylene, perchloroethylene, various pesticides, various herbicides, and any other chemical deemed to be bioremediable.

In situ—The term "in situ" means in place.

Remediation—The term "remediation" means to change the physical or chemical composition of a contaminant in the soil or water.

Electron Donor—The term "electron donor" means a chemical composition that is capable of donating electrons, such as reduced transition metals, sulfur, and organic substances.

Electron Acceptor—The term "electron acceptor" means a chemical composition that is capable of accepting electrons such as oxygen, nitrate, ferric iron or other oxidized transition metals.

Treatment or Remediation Zone or Remediating a Zone—The terms "treatment zone or remediation zone or remediating a zone" means a volume in the ground which has been filled with a treatment composition.

Delivery control—The term "delivery control" is defined as a means that allows control of the rate a substance is delivered such means including co-precipitation, diffusion, or timed release coating.

Co-precipitation—The term "co-precipitation" means a method wherein desired substrates are delivered to the remediation zone as precipitates that dissolve at a controlled rate.

Diffusional Path Tortuosity—The term "diffusional path tortuosity" means a complex flow path within a particle wherein the complexity of the structure of the particle affects the rate of diffusion of a desired substance into the remediation zone.

Timed Release Coating—The term "timed release coating" means a substance that surrounds a solid particle and that dissolves at a particular rate to release the contents of the particle, the rate dependent on the thickness of the coating. Examples of timed release coatings that can be used to control the time the contents of a particle are released in a bioremediation environment include polyethylene, polypropylene, polyacrylamide, ethylene, propylene copolymer, ethylene vinyl acetate copolymer, vinylidene chloride, vinyl chloride, vinylidene chloride-vinyl chloride copolymer, polystyrene, and biodegradable polymers such as agarose.

Bead—The term "bead" means a particle or substance having a round or irregular shape that can be made of clay, a polymer, or comprised of an innocuous oil such as cotton seed oil or corn oil that has been hydrogenated to make the oil a solid.

Microporous particle—The term "microporous particle" means a bead or particle having a round or irregular shape that has micropores or microfissures or channels throughout defining a matrix, the micropores or microfissures being necessary for adsorbing the desired substance and being capable of delivering the desired substance wherein the rate of delivery is dependent on the size of the microporous particle, and the complexity of the structure of the particle wherein the size and number of the micropores or microfissures, and the interconnectedness or matrix of the micropores or microfissures throughout the particle affect the complexity of the particle's structure. Microporous particles can be produced from compounds such as clay or polymers.

Particle—The term "particle" means a solid substance either a bead having either a round or an irregular shape that can be made of clay, hydroxy apatite, a polymer, or a hydrogenated innocuous oil.

Innocuous oil—The term "innocuous oil" means any oil that is non-toxic.

Microorganism—The term "microorganism" means any microbial species such as bacteria, yeast, or fungi known or further discovered (e.g. such as mixtures of microorganisms present in and isolated from natural flora) that is capable of metabolizing a toxic chemical or compound. Examples of microorganisms that are useful, include but are not limited to, *Pseudomonas stutzeri* strain KC, *Nocardia salmonicolor, Nocardia globerula, Nocardia paraffinae, Nocardia poaca, Pseudomonas putida, Pseudomonas oleovorans, Pseudomonas aeruginosa, Pseudomonas fluoroscens, Mycobacterium phlei, Mycobacterium lacticola, Mycobacterium paraffinicum, Aerobacter aerogenes, Bacillus subtilis, Sacharomyces cereviseae, Bacterium acidipropionci, Bacterium aliphaticium liquifaciens, Arthrobacter paraffinens, Rhodococcus rhodochrous, Acinetobacter calcoaceticus*, the various Azotobacter sp., Bacillis sp., Clostridium sp., Fusarium sp., Candida sp., Flavobacterium sp., Corynebacterium sp., Achromobacter sp. Acinetobacter sp., Rhodococcus sp., Pseudomonas sp., Mycobacterium, Nocardia sp., Rhodotorula sp., filamentous fungi such as Penicillium sp. and Phycomyces sp., and Apergillus sp., *Streptomyces griseus*, among others. Further, the term "microorganism" means naturally occurring fauna in the soil. Further still "microorganism" means microorganisms that have been genetically engineered to metabolize or improve its ability to metabolize toxic chemicals and compounds. Finally, microorganism may mean enzymes that can degrade unwanted chemicals.

Nutrient medium—The term "nutrient medium" means any nutrient that supports growth of a microorganism. Examples of nutrient media include but are not limited to biological buffers, carbon sources, electron donors, alkalinity causing agents, electron acceptors such as ferric iron or nitrate, energy sources such as glucose, and compounds produced by one microorganism that induce a second microorganism to remediation activity.

Metabolizable Chemical—The term "metabolizable chemical" means any chemical modified by a microorganism.

Environmental Amendments—The term "environmental amendments" means any chemical, biological or microorganism that is introduced into the environment.

In situ remediation has the potential for providing low cost treatment options for environments contaminated with hazardous wastes. The biological treatment options provide a means of treating hazardous materials without the need for extraction or evacuation of contaminated materials. Bioremediation (both biostimulation and bioaugmentation) requires periodic or continuous introduction of nutrients or buffers to sustain active populations of bacteria, capable of degrading hazardous wastes in situ. For treatment of many sites, delivery of nutrient(s) or other environmental modifiers may be needed over sustained periods of time. The present invention provides an inexpensive means of delivering controlled levels of nutrients to maintain active microorganism populations, or chemical reactants to effect degradation over extended periods of time. This is performed by delivering a particle capable of delivering via dissolution the nutrients, environmental modifiers and/or reactants capable of biologically remediating an environment contaminated with hazardous materials.

Polymer—The term "polymer" means any compound that has been polymerized to form a rigid structure and such compounds may be manufactured from polyethylene, polypropylene, polyacrylamide, ethylene, propylene copolymer, ethylene vinyl acetate copolymer, vinylidene chloride, vinyl chloride, vinylidene chloride-vinyl chloride copolymer, polystyrene, and biodegradable polymers such as agarose.

In situ remediation has the potential for providing low cost treatment options for environments contaminated with hazardous wastes. The biological treatment options provide a means of treating hazardous materials without the need for extraction or evacuation of contaminated materials. Bioremediation (both biostimulation and bioaugmentation) requires periodic or continuous introduction of nutrients or buffers to sustain active populations of bacteria, capable of degrading hazardous wastes in situ. For treatment of many sites, delivery of nutrient(s) or other environmental modifiers may be needed over sustained periods of time. The present invention provides an inexpensive means of delivering controlled levels of nutrients to maintain active microorganism populations, or chemical reactants to effect degradation over extended periods of time. This is performed by delivering a solid phase material capable of delivering via dissolution the nutrients, environmental modifiers and/or reactants capable of biologically remediating an environment contaminated with hazardous materials.

A novel feature of this invention is the use of control of diffusion rates of the delivered substrates to achieve desired in situ concentrations. The delivery control is achieved by 1) selection of appropriate chemical forms of the needed substrates with environmentally compatible initial dissolution properties, which initial properties are further enhanced by 2) use of porous particle matrices to control surface area for diffusion delivery, and 3) use of time dissolving or condition specific dissolving coatings of particles to control serial release of substrates over long time duration or with appropriate delivery cycle. These mechanisms will allow control of contact time of the delivered substrate in the environment.

The invention provides a series of particle formulations to achieve process specific delivery of the required substrates to effect bioremediation. These could include, microorganisms, nutrients, and any other substrates that are necessary for biological in situ remediation of hazardous waste. Any potential combination of required substrates could be delivered if a suitable carrier bead or formed bead of sufficient compression strength and appropriate size can be achieved.

Current means capable of introducing the particles of the present invention are 1) jet grout drilling introduction, 2) rotary hollow stem auger/trimmie slurry introduction, 3) hydraulic fracturing and 4) freeze placement. Jet grouting utilizes high pressure delivery into the subsurface to "fluidize" the formation and allow introduction of materials. Rotary hollow stem/trimmie placement involves pumping slurried materials into the subsurface annulus of the borehole. Hydraulic fracturing utilizes low pressure delivery of a slurry to create vertical or horizontal fractures in the subsurface. Hydraulic fracturing will enable delivery of the particles of the present invention when lower shear and pressures are needed to preserve particle integrity. Freeze wall placement would allow direct introduction of the particles of the present invention into a confined zone of the subsurface.

An object of the present invention is particle formulations that achieve delivery control by means of co-precipitation, wherein the substrates are delivered as a controlled solubility precipitate. This process can utilize hydrogenated cotton seed oil spheres or beads or particles of the present invention which are produced by Aveka, Inc. (Minneapolis, Minn.) to deliver carbon to support growth and carbon tetrachloride degradation by *Pseudomonas stutzeri* strain KC. These solid beads may also be formulated with hydrogenated derivatives of other innocuous oils, an example being hydrogenated corn oil. The solid oil beads may range in size from 10 $\mu$m to 3 mm in diameter. The preferred size of beads demonstrated in Example 2 was approximately 300 microns in diameter. The size of the solid oil beads determines the length of time the carbon source provided by beads will persist and supply carbon to the microorganisms. Large beads will provide a carbon source for the microorganisms for a longer period of time than smaller beads. This makes it possible to control the length of time the carbon source is to be provided to the microorganisms simply by adjusting the size of the beads. For long duration remediation zone projects the beads will be larger than beads used for short term remediation zone projects.

The use of the solid oil beads of the present invention are an improvement over prior art methods of providing oil to the soil in liquid form because the liquid oil rapidly dissipates, thereby losing its effectiveness as a carbon source for the microorganisms and the rapid depletion of the oil can result in the generation of unwanted degradation by-products. For long term remediation zone projects, at additional expense, liquid oil would have to be periodically reinjected into the site to maintain a carbon source for the microorganisms.

Additional particle formulations of the present invention to achieve delivery control include control of diffusional path tortuosity, which is a means for limiting the rate of diffusion of a desired substrate by requiring diffusion via of a complex flow path from within a particle. This process can utilize microporous clay beads or particles of the present invention which are manufactured by Einfach-Grün Hydroton (Eschborn, Germany) to deliver to a remediation zone either simultaneously or differentially such substances may be a carbon source, an electron donor, nutrients, such as phosphate, an electron acceptor, an acidity or alkalinity source such as potassium phosphate for pH control, and microorganisms. These microporous beads may also be manufactured from polymers, preferably polymers that are biodegradable. The preferred size of microporous clay beads ranged in size from 4 mm to 8 mm. The pores of the beads may be as narrow as 0.22 $\mu$m; however, for most purposes the pores will be greater than 1 $\mu$m. The complex flow path of the microporous beads may be interconnected micropores, channels or microfissures or both throughout the bead. The smaller and more complex the micropore network the slower the rate of diffusion. Additionally, the larger the particle size, the more material that can be contained therein, and the longer the microporous beads may provide their contents to the soil. Furthermore, microporous beads have a high compression strength and therefore may be applied to a remediation zone using high pressure application methods.

The microporous beads of the present invention are an improvement over prior art methods for remediation in that beads containing a carbon source, beads containing microorganisms, beads containing nutrients, such as phosphates, beads containing an electron acceptor source such as ferric iron, beads containing an electron donor, such as sulfur, and beads containing an alkalinity or acidity source for pH control may all be provided simultaneously or differentially to a remediation zone. Providing microporous beads that enable control of pH is of particular importance in that a niche that is capable of supporting the desired microorganism for degrading a contaminant can be achieved in an environment containing a diverse flora of microorganisms. For example, adjusting the pH of an environment with an alkali such as KOH and then introducing *Pseudomonas stutzeri* strain KC into the environment, allows the introduced *P. stutzeri* KC to compete more effectively against the indigenous microorganisms for nutrients and allowing *P. stutzeri* to express activities, such as the activity for breaking down carbon tetrachloride to carbon dioxide, in the presence of indigenous soil microorganisms. Introducing an alkali to change the pH of the site to be remediated increases the effectiveness of bioremediation and in some cases may accelerate the bioremediation process.

Current means of introducing remediation agents into contaminated environments include injection of liquid or gas phase components into subsurface environments, extraction of liquid or gas phase components and treatment ex situ, or excavation of contaminated solids. These options are all expensive, both for installation of the injection/extraction systems, and for the operation. In the present invention delivering nutrients or reactants which slowly dissolve in situ, eliminates or reduces the capital costs of drilling and installing wells, pumping systems, or barriers to direct flow. The present invention allows the establishment of a permeable reaction "curtain", or reaction wall to be introduced in the path of a contaminant plume. The reaction curtain is constructed so as to allow unimpeded flow of contaminated groundwater while ensuring sufficient contact with the agents of remediation. Various construction methods, such as jet grouting or vertical hydraulic fracturing, can be employed for placement of the remediation agents of the present invention.

To effect remediation the preferred process of the present invention provides for the loading of porous beads or cotton seed oil beads with desired environmental amendments and injecting the loaded solid phase material into the contaminated environment to intercept the path of the contaminant with a permeable reaction curtain containing the desired biological or chemical components.

In the following Examples, all chemicals used were ACS reagent grade. All water used in reagent preparation was 19 Mohm resistance or greater. $CCl_4$ (99%—purity) was obtained from Aldrich Chemical Co., Milwaukee, Wis. $^{14}C$-labeled $CCl_4$ (3.4 mCi/mMol) was obtained from NEN DuPont (Boston, Mass.). Carbon tetrachloride was monitored by gas chromatography as previously described (Tatara et al, "Applied Environmental Microbiology", Vol. 59, pages 2126–2131 (1993). Anions were determined by ion chromatography (EPA Method 300). pH was measured with an Orion 701 pH meter. Protein was determined by the modified Lowery method (Markwell et al, "Methods of Enzymology", Vol. 72, pages 296–301 (1981).

COMPARATIVE EXAMPLE 1

Microbial transformation of hazardous wastes can be effected by *Pseudomonas stutzeri* KC (DSM deposit no. 7136) (ATCC deposit number 55595; U.S. Pat. No. 5,602, 036) a denitrifying bacterium that converts carbon tetrachloride (CT) to carbon dioxide (40–50%) and non-volatile compounds (45–55%) without production of detectable chloroform under most growth conditions (Criddle et al, "Applied Environmental Microbiology", Vol. 56, pages 3240–3246 (1990); and Dybas et al, "Applied Environmental Microbiology", Vol. 61, pages 758–762 (1995). This experiment was to determine whether *P. stutzeri* KC could degrade carbon tetrachloride with minimal production of chloroform when vegetable oil was supplied as the carbon source. Vegetable oil was the source for the solid hydrogenated oil beads in the following Examples.

Figure 2:
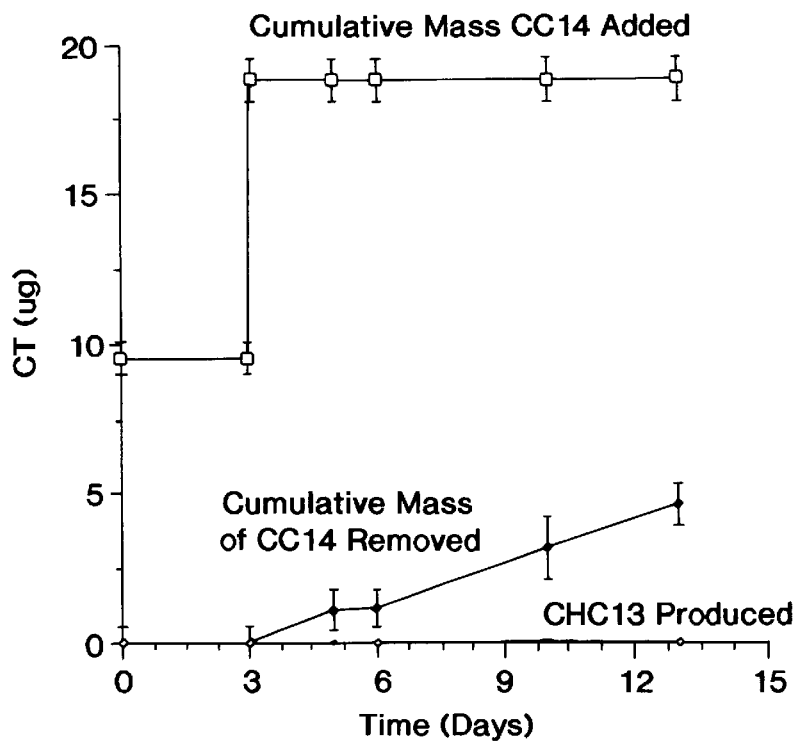
FIG. 2 is a graph showing the cumulative mass of $CCl_4$ removed and $CHCl_3$ produced by an enrichment of organisms from Schoolcraft aquifer solids. $CCl_4$ was added initially and on day 3. Error bars for the mass of $CCl_4$ added represent the cumulative error of addition. Error bars for experimental samples represent a standard deviation of three independently grown cultures. The graph shows that this microorganism is particularly effective.

SGW medium (acetate free) was prepared at pH 8.2 with 2× phosphate buffer (27.22 g/L $KH_2PO_4$). Ten milliliters of medium were dispensed into 20 mL automated head space sampler vials, and 50 μL of corn oil was added to each vial. Vials were degassed through the interlock of an anaerobic glove box and sealed under anoxic conditions using TEFLON® lined butyl rubber septa and aluminum crimp seals. Vials were autoclaved at 120° C. for 20 min. Carbon tetrachloride ($CCl_4$) was added from a sterile aqueous phase stock at a final mass of 9.5±0.6 μg. *P. stutzeri* KC was added as a 1% inoculum (v/v) from a 72 hour culture grown in SGW medium with corn oil as the electron donor under denitrifying conditions. It has been found that *Pseudomonas stutzeri* strain KC is capable of carbon tetrachloride degradation when grown on various vegetable oils. Natural flora from the carbon tetrachloride contaminated site at Schoolcraft, Mich. was added to a second set of vials. These $^{14}C$—$CCl_4$ studies revealed about 40–50% of the originally added $CCl_4$ was converted to $CO_2$ by *P. stutzeri* KC. Corn oil was used to evaluate the long term growth characteristics and $CCl_4$ transformation capacity of *P. stutzeri* KC and of a flora enrichment derived from $CCl_4$ contaminated aquifer solids from Schoolcraft, Mich. $CCl_4$ masses of 18.3±0.8 and 17.2±1.3 μg were removed by *P. stutzeri* KC and *P. stutzeri* KC combined with the Schoolcraft flora, respectively (FIG. 1). No significant $CCl_4$ transformation was observed for the Schoolcraft flora alone (FIG. 2). Only approximately 5% of the initially added $CCl_4$ was converted to chloroform ($CHCl_3$) by *P. stutzeri* KC. Growth curves, pH, and nitrate analysis revealed that the yield and rates of growth were limited by the supply of nitrate.

FIG. 1 shows that vegetable oil can support carbon tetrachloride removal by *P. stutzeri* KC, and that the system was limited only by the supply of the electron acceptor (nitrate). FIG. 2 shows that no significant carbon tetrachloride degradation was observed for the Schoolcraft flora alone when provided vegetable oil. While the data demonstrates that vegetable oil is sufficient to effect carbon tetrachloride degradation by *P. stutzeri*, the rate of dissolution of the oil is fairly rapid, which results in an excessively rapid utilization of the oil and the generation of fermentation products and noxious substances (such as $H_2S$) which adversely affects groundwater quality. To mitigate this problem the dissolution rate of any added carbon must be such that the level in solution does not exceed the rate of supply of electron acceptors such as nitrate or oxygen which sustain degradation without the production of noxious end products.

To limit the rate of dissolution and thereby prevent formation of unwanted byproducts, an approach was adopted that was based on the solid phase delivery/slow dissolution compositions of the present invention. The following Examples show: 1) hydrogenated cotton seed oil particles or beads, and 2) microporous heat fractured clay particles filled with base phosphate, vegetable shortening and microorganisms (*Pseudomonas stutzeri* stain KC), each in separate beads.

EXAMPLE 2

This Example shows that solid hydrogenated oil particles can support growth of *P. stutzeri* KC and effect degradation of carbon tetrachloride. Groundwater (10 ml) from a carbon tetrachloride impacted section of an aquifer located in Schoolcraft, Mich. were dispensed in sterile 20 ml vials (microcosms). Hydrogenated solid cotton seed oil beads (1.2 mg), nitrate (240 ppm) and carbon tetrachloride (10 ppm) were added to the microcosms. Microcosms were inoculated with 0.1% (v/v) strain KC culture grown in nutrient broth.

Figure 3:
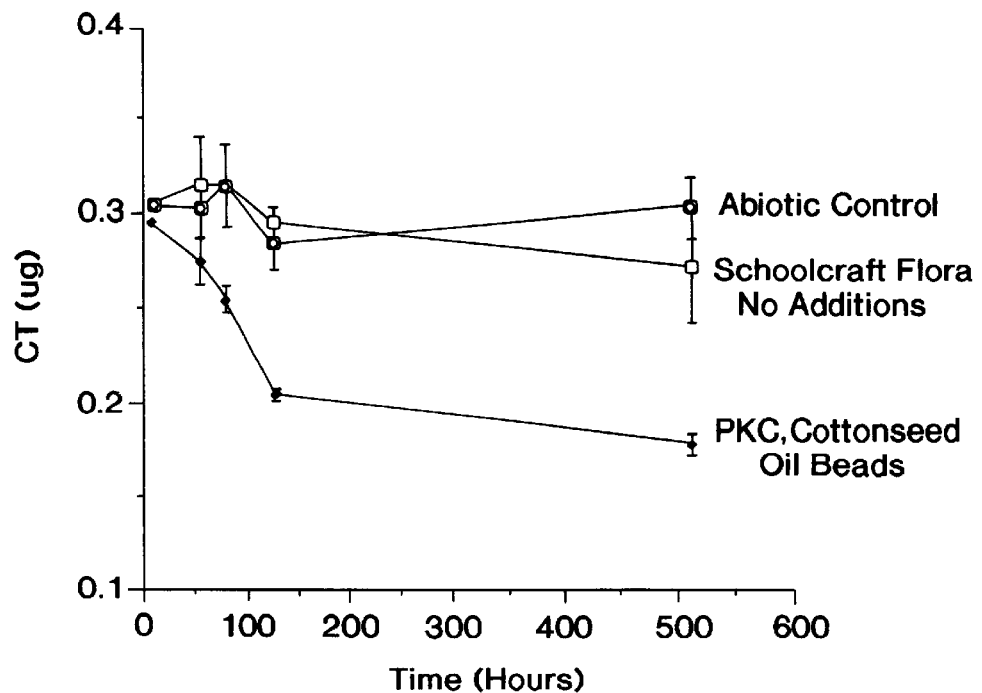
FIG. 3 is a graph showing the transformation of Carbon tetrachloride by *P. stutzeri* KC in aquifer solid/groundwater slurries when provided hydrogenated cotton seed oil beads by the method of the present invention.
Figure 4:
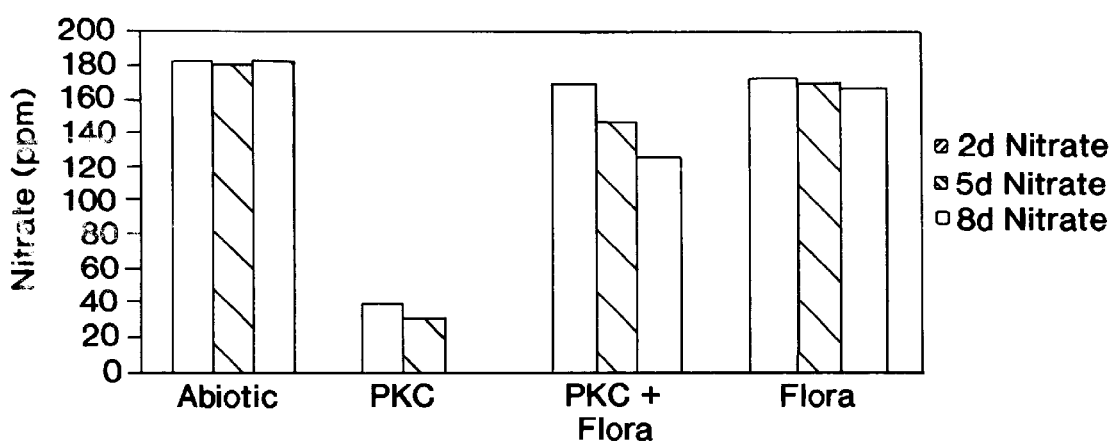
FIG. 4 is a graph showing nitrate removal by *P. stutzeri* KC when provided hydrogenated cotton seed oil beads as the carbon source.

The hydrogenated cotton seed oil particle system makes use of the calorie rich nature of an oil with a delivery system that controls solubility. Particles of hydrogenated cotton seed oil are shown to be capable of supporting carbon tetrachloride degradation by *P. stutzeri* KC. Aveka, Inc. produces solid particles of hydrogenated cotton seed oil in the 10 μm–3 mm diameter size range. The particles can be provided with differing solubilities to generate more effective time release. These particles are produced by a process involving melt spraying (prilling) to produce particles of the required size. 300 micron diameter beads were used in these experiments. FIGS. 3 and 4 show that the solid hydrogenated cotton seed oil beads of the present invention can support carbon tetrachloride removal by *P. stutzeri* when supplied with an electron acceptor such as nitrate (nitrate utilization). The indigenous flora under the same conditions did not degrade carbon tetrachloride (FIG. 3) nor utilize the nitrate (FIG. 4). This experiment shows that the solid hydrogenated oil beads of the present invention are an effective source of carbon for $P.$ $stutzeri$ KC and will support $P.$ $stutzeri$ KC degradation of carbon tetrachloride.

EXAMPLE 3

A porous bead controlled delivery system of the present invention was tested for ability to support carbon tetrachloride degradation by $P.$ $stutzeri$. In these experiments, microporous heat fractured clay beads were used to deliver base, phosphate, acetate, vegetable shortening and Pseudomonas strain KC bacteria to environmental samples contaminated with carbon tetrachloride.

The microporous clay particles are manufactured by Einfach-Grün Hydroton (Eschborn, Germany). These particles are produced by heat fracturing clay beads to produce beads of low (0.6 g/ml) dry density which possess excellent capillary action, allowing uptake of liquid.

For all experiments particles (4 to 8 mm diameter) were washed 3 times with 18 Mohm resistance deionized water. To wash the internal pore structure, beads (40–100 g) were placed in 1 liter deionized water, and a vacuum applied (25" Hg) for 5 minutes to degas particles. The water was exchanged 3 times, then particles were dried at 100° C. Four different types of beads were produced.

1. Organic carbon loading of microporous particles. For carbon tetrachloride degradation studies, 8 mm clay particles were washed and dried as described above. Particles (40 g) were added to molten vegetable shortening (CRISCO®, 300 g) at 60° C. The particle/shortening slurry was then subjected to a vacuum (25: Hg) to degas internal pores and allow molten shortening to fill the particle. Particles were removed from the molten oil with sterile forceps and stored in sterile test tubes at room temperature. A loading of 170 mg shortening oil per gram particle was achieved. Each bead (average loaded mass 0.5 g) contained 85 mg shortening.

2. pH buffer—rapidly soluble base loading of microporous particles. 8 mm clay particles (20 g) were added to 300 ml 3 M KOH solution. The slurry was then subjected to vacuum (25" Hg, 3 minutes) to allow degassing of internal pores and replacement with KOH solution. The particles were then dried 24 hours at 100° C. A loading of 1.77 mMol KOH per gram particle was achieved.

3. Phosphate and slowly soluble base loading of microporous particles. 8 mm clay particles (20 g) were added to 300 ml solution of 300 mg/l $Ca(OH)_2$, 30 mg/l $PO_4$ (freshly made). The slurry was then subjected to vacuum (25" Hg, 3 minutes) to allow degassing of internal pores and replacement with the solution. A loading of 0.14 mg $Ca(OH)_2$ and 0.014 mg $PO_4$ per gram particle was achieved.

4. Microbial loading of microporous particles. 8 mm clay particles (40 g) were added to a 4 hour nutrient broth of a grown $P.$ $stutzeri$ KC culture. After addition of the beads, growth with 150 rpm shaking, at 20° C. was continued for an additional 18 hours. Particles were air dried aseptically for 48 hours. A batch of the particles were extracted with cell extraction buffer (Fletcher et al, "Applied Environmental Microbiology", Vol. 58, pages 2954–2959 (1992)) to determine the loading efficiency of the above process. A loading level of $2.5 \times 10^7$ colony forming units (cfu) of $P.$ $stutzeri$ KC per gram of particles was observed using the above loading process.

5. Experiment. To test the loaded particles for effectiveness at carbon tetrachloride degradation, aquifer solids (40 g (wet weight)) from the Schoolcraft, Mich. site and 200 ml groundwater from the same site were dispensed into autoclaved bottles and carbon tetrachloride was added to 65 ppm. The groundwater contained nitrate at 69 ppm. The following particles were added to each complete microcosm 1) 0.5 g particle delivering 85 mg shortening carbon 2) two 0.5 g particles delivering 1.77 mMol KOH 3) two 0.5 g particles delivering 0.14 mg $Ca(OH)_2$ and 0.014 mg $PO_4$ and 4) a 0.5 g particle delivering $1.25 \times 10^7$ cfu $Pseudomonas$ $stutzeri$ strain KC.

Figure 5:
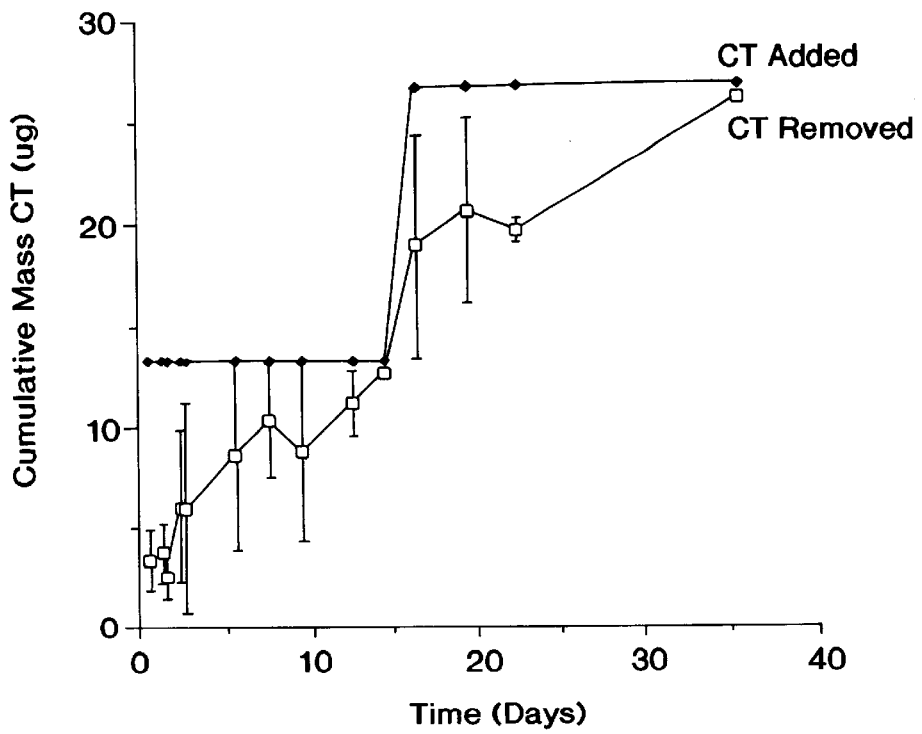
FIG. 5 is a graph showing Carbon tetrachloride degradation by *P. stutzeri* KC grown on microporous beads of the present invention which provide nutrients base, phosphate, acetate, vegetable shortening and strain *Pseudomonas stutzeri* KC and which are introduced into aquifer material/groundwater slurries via microprobes clay fractured beads.
Figure 6:
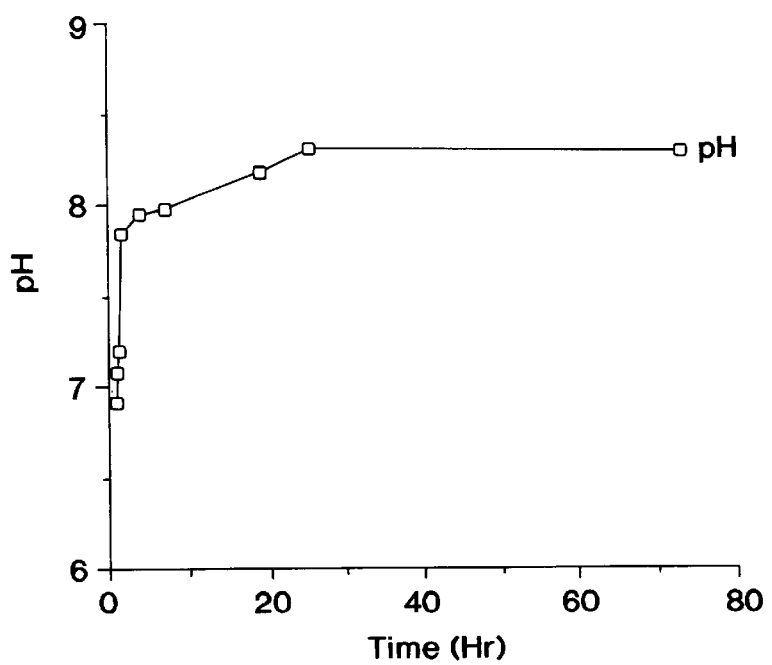
FIG. 6 is a graph showing the effect of the microporous beads on pH of aquifer material/groundwater slurries due to the base.

FIG. 5 shows that the particles can be used to successfully remediate environmental materials contaminated with carbon tetrachloride (FIG. 5) without significant $H_2S$ formation. FIG. 6 shows the effect of microporous bead delivered base on the pH of aquifer material/groundwater slurries. The pH was rapidly raised to approximately pH 8.2 and was maintained at that level for over 70 hours, providing the ideal environment for maximal $P.$ $stutzeri$ activity to effect efficient carbon tetrachloride degradation.

EXAMPLE 4

The following experiment tested the permeability effects of the microporous particles.

1. Preparation of Test Solids:

Ottawa Sand is sieved to isolate all particles retained by number 40 sieve. Measured fractions of 6–8 mm microporous beads are then mixed with the sieved Ottawa Sand. The solid mixture is washed in ultra-pure deionized water to remove impurities and placed in vacuum at 25 mm Hg for 3 minutes to degas the microporous particles. The Ottawa Sand and microporous bead mixture is pasteurized for 24 hours prior to packing in the column.

2. Column Preparation:

The column utilized is pasteurized for 24 hours prior to packing. Ottawa Sand and microporous particle mixtures are saturated packed to reduce entrapped air. Material is packed in 5 equal layers. Each layer is tamped 25 times with 1.2 kg hammer.

3. Falling-Head Permeability Tests:

A standard falling head permeability test is utilized to measure the permeability coefficient, k, of the Ottawa Sand and clay particle mixture. The time is measured for a column of water to fall a determined height and related to the permeability by the following equation:

$$k = (aL/At) \ln(h_0/h_1)$$

k (cm/s): coefficient of permeability a ($cm^2$): cross-sectional area of stand pipe L (cm): length of column t (sec.): time required for column of water to fall A ($cm^2$): cross-sectional area of column $h_0$ (cm): initial height of water in stand pipe $h_1$ (cm): final height of water in stand pipe 4. Data Reduction A total of 5 columns are packed for each microporous particle fraction. Every column is weighed and oven dried to determine water content and porosity of Ottawa Sand and clay bead mixture. The permeability coefficients for each column are determined and averaged to yield one average k value for a given microporous particle fraction. A 90% confidence interval is determined based on the t-distribution with 4 degrees of freedom.

Figure 7:
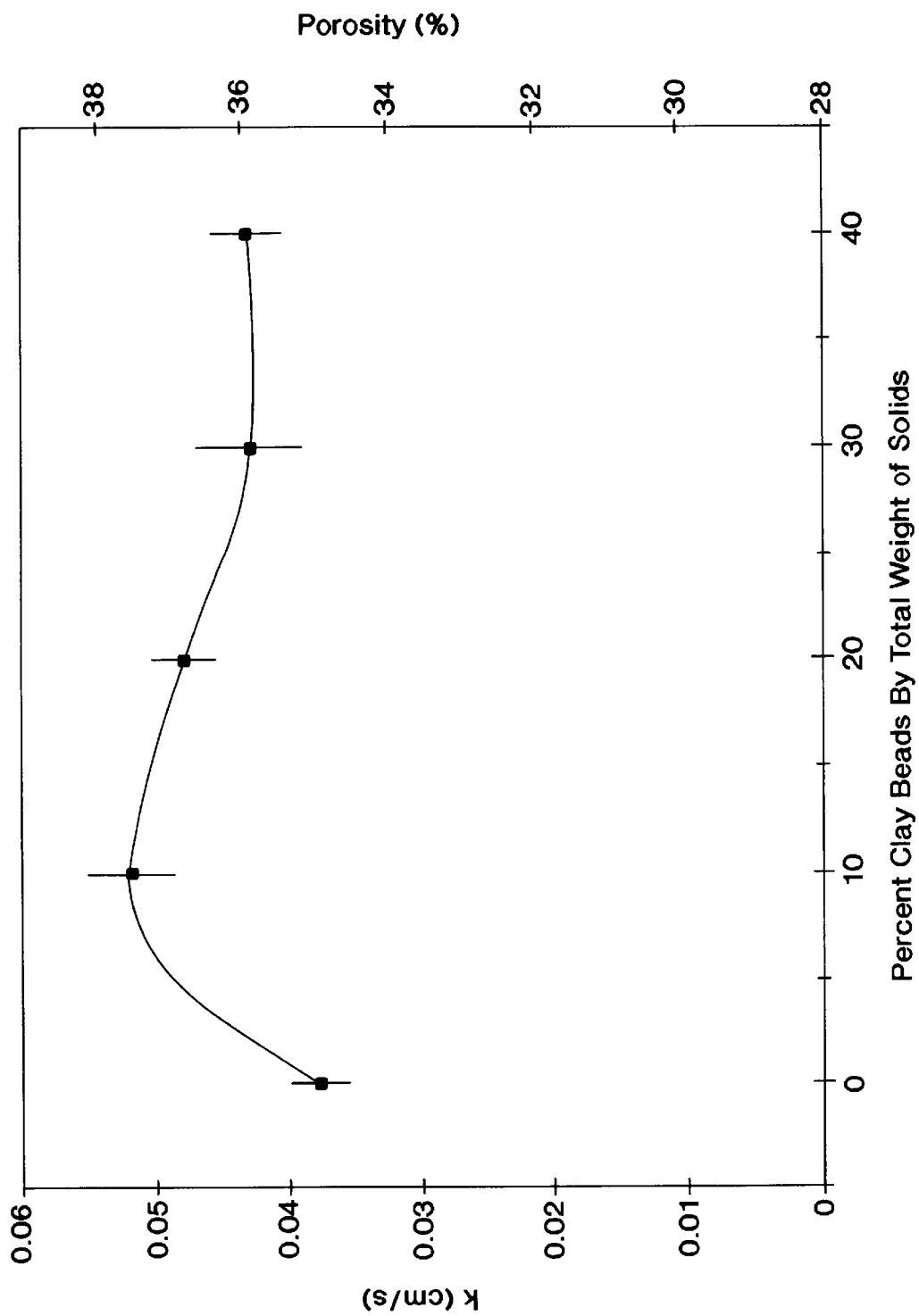
FIG. 7 is a graph showing the effect of microporous clay beads on the fluid conductivity of sand.

FIG. 7 shows the effect of microporous particles on the conductivity of sand as measured by the falling-head permeability test for different percentages by weight of beads.

The figure shows that the k rises from approximately 0.03 at 0 percent by weight beads to a maximum of 0.05 at 10 percent by weight of beads and then falling to approximately 0.04 at 40 percent by weight of beads.

EXAMPLE 5

This experiment was to determine the kinetics of the release of organic carbon from the microporous particles.
1. Preparation and Loading of Particles.

Particles were washed and dried as described in Example 3. Molten vegetable shortening (CRISCO®) was added to the dry particles. Particles and shortening were set in a 60° C. oven. After a day of loading the remaining shortening was decanted and the particles were blotted dry. A loading level of 0.197 g shortening per bead was achieved.
2. Kinetics of organic Carbon Release from Particles.

Figure 8:
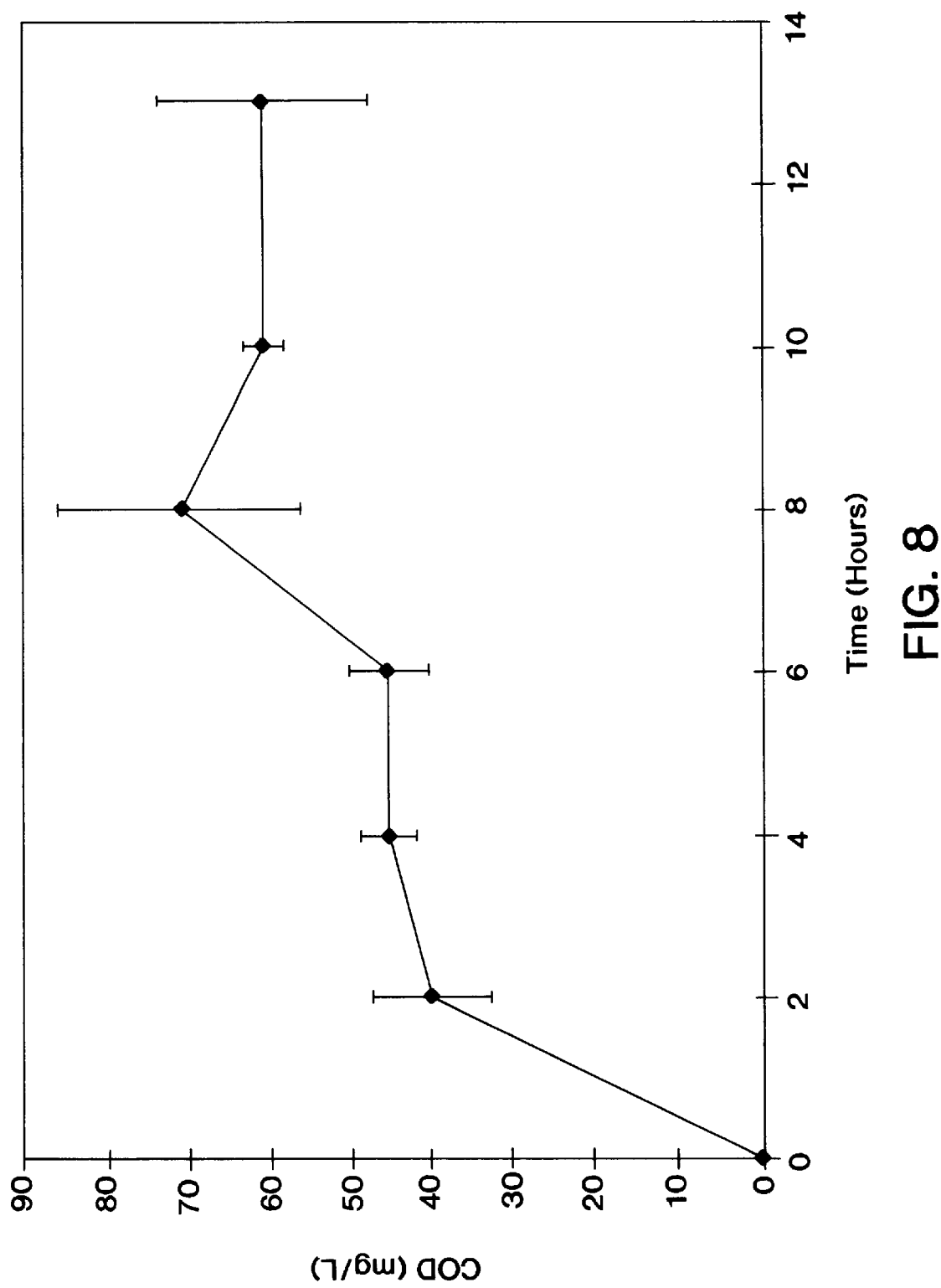
FIG. 8 is a graph showing concentration of carbon in the liquid with time using beads impregnated with vegetable oil (values represent average of triplicates, error bars represent standard deviation).

Clay particles loaded with shortening as described above were shaken in vials containing 15 ml of deionized water at 150 rpm. Liquid samples were taken and the amount of organic carbon determined by Chemical Oxidation Demand (COD) measurements. A plot of COD versus time is shown in FIG. 8. After approximately 12 hours a liquid phase concentration of 60 ppm carbon was obtained. After an initial rapid release of carbon, the bulk solution concentration of carbon appeared to stabilize at 60 ppm.

EXAMPLE 6

In some environments, toxic metals, such as chromium copper, zinc or cadmium, can limit the efficacy of bioremediation achievable using the slow-release particles. In such environments, additional particles were added to the slow-release composition to enable the removal of the toxic metals from solution. Examples of such particles include ion exchange beads, zeolite minerals with high ion exchange capacity, or other chelating particles.

EXAMPLE 7

In some environments, it is desirable to increase the concentration of sorbed organics within the bioreactive zone including the slow-release composition. For example, some organics may be toxic at high aqueous concentration and rapid removal from the water phase can facilitate remediation. In other cases, it is desirable to concentrate organics that slowly degrade to increase their residence time within the treatment regime. For the above cases, particles that sorb organics, such as ion exchanged modified clays (U.S. Pat. No. 5,268,109) or activated carbon particles can be included in the slow-release composition.

EXAMPLE 8

Delivery of slowly dissolving substrates can be more controlled when above-ground bioreactors are employed or when the particles are enclosed within cartridges or cassettes which are installed within the treatment regime and periodically removed for replenishment or reactivation.

In some instances, the microorganism colonizes the particle. This is particularly the case with the inert beads containing the nutrient medium.

It is intended that the foregoing description be only illustrative of the present invention and that the present invention be limited only by the hereinafter appended claims.

We claim:

1. A composition which comprises an admixture of multiple particles which are water insoluble with micropores throughout each of the particles, the micropores of at least one particle of a second group of particles containing a microorganism and the micropores of at least one particle of a first group of particles containing a chemical selected from the group consisting of an electron acceptor, an electron donor, substances for modification of pH, a nutrient medium for the microorganism and mixtures thereof, wherein said chemical is exposed on a surface of said at least one particle and further is releasable over time in situ in an aqueous environment to the particles containing the microorganism.

2. The composition of claim 1 wherein the particles are comprised of a microporous clay.

3. The composition of claim 1 or 2 wherein said microorganism is Pseudomonas KC strain ATCC 55595.

4. A composition which comprises particles in admixture which are water insoluble with micropores throughout the particle, (a) the first group of the particles containing a chemical in the micropores metabolizable by a microorganism which is exposed on a surface of the particles, wherein the particles release said chemical into the water over a period of time to the microorganism in the presence of the water; and (b) a second group of the particles containing a microorganism in the micropores.

5. The composition of claim 4 which contain a nutrient medium as the chemical in the first group of the particles.

6. The composition of claim 4 wherein the first group of the particles contain an electron donor or an electron acceptor as the chemical.

7. A composition for providing a chemical to a microorganism over time in the presence of water which comprises:

(a) inert and water insoluble particles having multiple channels throughout the particle which are less than about 0.1 to 100 microns in average diameter and having a size of about 0.1 to 50 millimeters; and (b) a chemical provided in the channels in a first group of the particles which is metabolizable by the microorganism, wherein said chemical is exposed on a surface of the particles and is released over time from the particles into the water to be metabolized by the microorganism; and (c) the microorganisms in the channels of a second group of the particles which metabolize the chemical.

8. The composition of claim 7 wherein the chemical is selected from the group consisting of an electron acceptor, an electron donor, substances for modification of pH, a nutrient medium for the microorganism and mixtures thereof.

9. The composition of claim 7 wherein said microorganism is Pseudomonas KC strain ATCC 55595.

10. The composition of claim 7 containing a nutrient medium for the microorganism as the chemical in the first group of the particles which is exposed on a surface of the particles.

11. The composition of claim 10 wherein the particles contain an electron donor or an electron acceptor.

* * * * *

UNITED STATES PATENT AND TRADEMARK OFFICE
CERTIFICATE OF CORRECTION

PATENT NO.     : 6,331,300 B1                                                      Page 1 of 1
DATED          : December 18, 2001
INVENTOR(S)    : Michael J. Dybas, Craig S. Criddle and Michael E. Witt It is certified that error appears in the above-identified patent and that said Letters Patent is hereby corrected as shown below:

Column 6,
Line 3, "Apergillus" should be -- Aspergillus --.

Column 8,
Line 12, "of" after "via" should be deleted.

Column 11,
Line 50, "3 minutes" should be -- 30 minutes --.

Column 12,
Line 30, "3 minutes" should be -- 30 minutes --.

Column 14,
Line 5, "of a second group of particles" should be -- of a first group of particles --; and Lines 6 and 7, "of a first group of particles" should be -- of a second group of particles --.

Signed and Sealed this

Twentieth Day of August, 2002

Attest:

JAMES E. ROGAN
Attesting Officer                    Director of the United States Patent and Trademark Office